United States Patent [19]

Chamberlin, Sr.

[11] Patent Number: Plant 6,992

[45] Date of Patent: Aug. 22, 1989

[54] PEACH TREE "MAY SUN"

[75] Inventor: Thomas O. Chamberlin, Sr., Visalia, Calif.

[73] Assignees: Metzler Investments; Metropolitan Life Insurance Company, both of Del Rey, Calif.

[21] Appl. No.: 234,618

[22] Filed: Aug. 22, 1988

[51] Int. Cl.[4] ..... A01H 5/00

[52] U.S. Cl. ..... Plt./43

[58] Field of Search ..... Plt./43

*Primary Examiner*—Robert E. Bagwill

*Attorney, Agent, or Firm*—Worrel & Worrel

[57] ABSTRACT

A new and distinct variety of peach tree which is characterized by a date of maturity of approximately May 20 to May 25 under the ecological conditions prevailing at Del Rey, Calif., in the central part of the San Joaquin Valley of California, and which further is distinguished as to novelty by producing fruit which have a noteworthy flavor and desirable handling characteristics.

1 Drawing Sheet

BACKGROUND OF THE NEW VARIETY

The present invention relates to a new and distinct variety of Peach Tree hereinafter denominated varietally as "May Sun" and which is generally similar in its overall physical characteristics to the June Lady Peach Tree (U.S. Plant Pat. No. 3,022), of which it is a newly found second generation seedling, but from which it is distinguished therefrom and characterized principally as to novelty by bearing fruit which are ripe for commercial harvesting and shipment apporoximately May 20 through May 25 under the ecological conditions prevailing in the San Joaquin Valley of Central California and which further produces fruit which have a good flavor and excellent shipping and storage characteristics.

In a continuing effort to upgrade the quality of his employer's fruit products, the inventor is constantly on the alert to locate any new varieties that may appear from time to time as chance seedlings or mutations in the commercial orchards under his supervision and control. In connection with these labors, the applicant, in 1977, discovered a second generation chance seedling which originated from a June Lady Peach Tree (U.S. Plant Pat. No. 3,022), in the cultivated area of his employer's seedling Lot #20 which is located on the southwest corner of Jefferson and Del Rey Aves. near his employer's business address of 5286 South Del Rey Ave. in Del Rey, Calif.

ORIGIN AND ASEXUAL REPRODUCTION OF THE NEW VARIETY

The present variety of peach was a second generation chance seedling which originated from a June Lady Peach Tree (U.S. Plant Pat. No. 3,022), and which was discovered within cultivated area of Seedling Lot #20, under the ownership and control of the H. P. Metzler & Sons Company of Del Rey, Calif. The subject variety was observed at that time to have desirable characteristics and it was thereafter asexually reproduced by the inventor by removing buds from the original chance seedling and budding them into test seedlings which were later planted in a test plot located at 5286 South Del Rey Ave., in Del Rey, Calif. in 1979. These budded seedlings have been continually observed by the inventor and it has been subsequently determined that the progeny produced by these budded test seedlings possess the same distinctive characteristics as the original chance seedling.

The peach tree of the present invention is noteworthy in ripening approximately May 20 through May 25 under the ecological conditions prevailing at Del Rey, Calif. and further is characterized as to novelty by being positively influenced by the cultural practice of girdling, the subject variety producing fruit which mature earlier and do not have split pits, providing, however, that the girdling is accomplished at the appropriate time during the growing season.

BRIEF DESCRIPTION OF THE DRAWINGS

The accompanying drawing is a color photograph of a characteristic twig bearing typical leaves, five mature fruit showing their external coloration sufficiently mature for harvesting and shipment, one fruit of the subject variety dissected in the axial plane to illustrate the flesh coloration and a representative stone, all of the subject variety.

DETAILED DESCRIPTION

Referring more specifically to the pomological details of this new and distinct variety of peach tree, the following has been observed under the ecological conditions prevailing at the orchard of the inventor's employer which is located in Del Rey, Calif. All major color code designations are by reference to the Inter-Society Color Council, National Bureau of Standards. Common color names are also employed occasionally.

TREE

Size:

*Generally.*—Average.

Vigor:

*Generally.*—Very vigorous.

Productivity: Very good.

Regularity of bearing: Regular.

Trunk:

*Size.*—Average.

*Surface texture.*—The subject variety displays normal peach bark.

*Lenticels.*—Numbers — Average, having approximately 18-20 lenticels per square inch.

*Color.*—Bark — Yellowish-brown, (81 d. gy. y. Br.).

Branches:

*Size.*—Average.

*Surface texture.*—Average.

*Color.*—Brown, (81 d. gy. y. Br.).

*Lenticels.*—Numbers — Approximately 18–20 per square inch. Size — Average.

LEAVES

Size:

*Generally.*—Average.

*Length.*—Approximately seven to eight inches (177.8 mm.–203.3 mm.).

*Width.*—Approximately 1¾"–2", (44.25–50.8 mm.).

*Shape.*—Lanceolate.

*Color.*—Upper Surface — Green (125 m. 01. G.). Lower Surface — a lighter shade of green, (125 m. y. G.).

*Marginal form.*—Generally — Serrate.

Petiole:

*Length.*—Approximately 5/16" to ⅝" (7.938 mm.–15.875 mm.).

*Thickness.*—Approximately 1/16" to 3/32", (1.588 mm.–2.381 mm.).

Stem glands:

*Numbers.*—Variable, the subject variety may display one or two pair of stem glands, depending upon the size of the leaf inspected.

*Position.*—The stem glands are found in pairs on each side of the stem and at the base of the leaf.

*Size.*—Generally — Average, however, they will vary in size in direct proportion with the size of the leaf.

*Type.*—Reniform.

*Color.*—Green, approximately (102 m. g. Y.).

Flower buds:

*Size.*—Generally — Small when observed at the red bud stage.

*Length.*—Approximately ¼", (6.35 mm.).

*Diameter.*—Approximately 3/16", (4.762 mm.).

*Shape.*—Generally — Rounded and slightly elongated.

*Pistil.*—Position — The pistil and the stamen will be exposed, just prior to the full opening of the flower, in a position approximately ⅛" to 3/16" past the petal, (approximately 3.175 mm.–4.762 mm.).

Flowers:

*Date of bloom.*—The subject variety blooms approximately the end of February to as late as March 4 at Del Rey, Calif.

*Size.*—Generally — Small to average in size.

*Diameter of each petal.*—Approximately 3/16" (4.762 mm.).

*Length of each petal.*—Approximately ⅜", (9.525 mm.).

*Color.*—Petals — The outer edge of each petal is a dark pink, (254 v. p. R.); the center of each petal is a lighter pink, (247 s.p. Pk).

FRUIT

Date of maturity when described: Ripe for commercial harvesting and shipment approximately May 20 to May 25 at Del Rey, Calif.

*Girdling.*—The inventor has discovered that the subject variety "May Sun" reacts positively to the cultural practice of girdling, the subject practice not causing the pits of the fruit to split.

*Date of girdling.*—The inventor has discovered that the best date to girdle the subject variety is approximately 30 to 35 days after the variety achieves 90% of full blossom.

*Effect of girdling.*—Girdling the subject variety increases the size of the fruit produced thereby and will accelerate the harvesting date of same.

*Uniformity*—Noteworthy, the fruit produced is uniformly round and has a base of medium width and an almost flat apex area.

*Size.*—Axial diameter — Approximately 2½" to 3¼", (63.5 mm.–82.5 mm.). Diameter — Transverse in the suture plane — Approximately 2⅝", (66.6 mm.). Diameter — Transverse at right angles to the suture plane — Approximately 2½" to 2¼", (63.5–82.5 mm.).

Form:

*Uniformity.*—Good.

*Symmetry.*—Symmetrical.

*Suture.*—The suture appears as a smooth and distinct line which extends from the base to the apex and is approximately 3¾" in length, (95.2 mm.).

Ventral surface:

*Shape.*—Rounded, and occasionally slightly flat.

Stem cavity:

*Shape.*—Rounded, and approximately ⅜" deep, (9.52 mm.).

Base:

*Shape.*—The base appears wide and slightly rounded.

Apex:

*Shape.*—Slightly rounded and may appear almost flat.

Pistil point: Very small and may appear receded.

Stem:

*Size.*—Average.

*Length.*—Approximately ⅜", (9.52 mm.).

*Thickness.*—Approximately 3/16", (4.762 mm.).

Skin:

*Thickness.*—Average.

*Texture.*—Generally — Smooth and tenacious to flesh.

*Color.*—Variable, dark red to bright yellow, (12 s. Red) to (17 v.d. Red) and (83. brill Y).

*Tendency to crack.*—Not observed.

*Pubescence.*—Light.

Flesh:

*Color.*—Yellow, (67 brill. OY).

*Juice production.*—Very juicy and slightly acidic.

*Aroma.*—Slight.

*Fibers.*—Not considered fibrous.

*Flavor.*—Noteworthy. Each peach has an excellent flavor.

*Ripening.*—Even.

*Eating quality.*—Exceptional

Stone:

*Generally.*—The stone of the subject variety is not a full freestone and therefore must be considered cling stone.

*Fibers.*—None evident.

*Size.*—Length — Approximately 1½", (38.1 mm.). Width — Approximately ⅞", (22.225 mm.).

*Thickness.*—Approximately 11/16", (17.46 mm.).

*Color.*—Generally — Yellow (71 m. OY.).

*Form*—Ovid.

*Base.*—Shape — Very small and flat.

*Apex.*—Shape — Pointed.

*Sides.*—Texture — Rough.

*Ridges.*—Size — Average in size and approximately 1/32" in depth, (0.79 mm.).

*Tendency to split.*—Providing that girdling of the variety is performed at the appropriate time, the tendency to split is slight.

*Use of the variety.*—Fresh market.

*Storage quality.*—Noteworthy, the subject variety has been kept in cold storage for periods in excess of 30 days with no deleterious effects noted.

*Shipping quality.*—Due in part to the firm nature of the flesh and the tough skin, the subject variety is expected to have noteworthy shipping characteristics.

Although the new variety of peach tree possesses the described characteristics when grown under the ecological conditions prevailing in Del Rey, Calif., in the Central part of the San Joaquin Valley, it is to be understood that variations of the usual magnitude and characteristics incident to changes in growing conditions, fertilization, pruning and pest control are to be expected.

Having thus described my new variety of peach tree, what is new and desired to be secured by Letters Patent is:

1. A new and distinct variety of peach tree substantially as illustrated and described and which is somewhat similar to the June Lady Peach Tree (U.S. Plant Pat. No. 3,022), from which it was derived as a chance seedling but from which it is distinguished therefrom and characterized as to novelty by bearing fruit which are ripe for commercial harvesting and shipment approximately May 20 through May 25 at Del Rey, Calif., and which further displays the desirable trait of being responsive to the cultural practice of girdling and produces fruit having desirable handling and shipping characteristics.

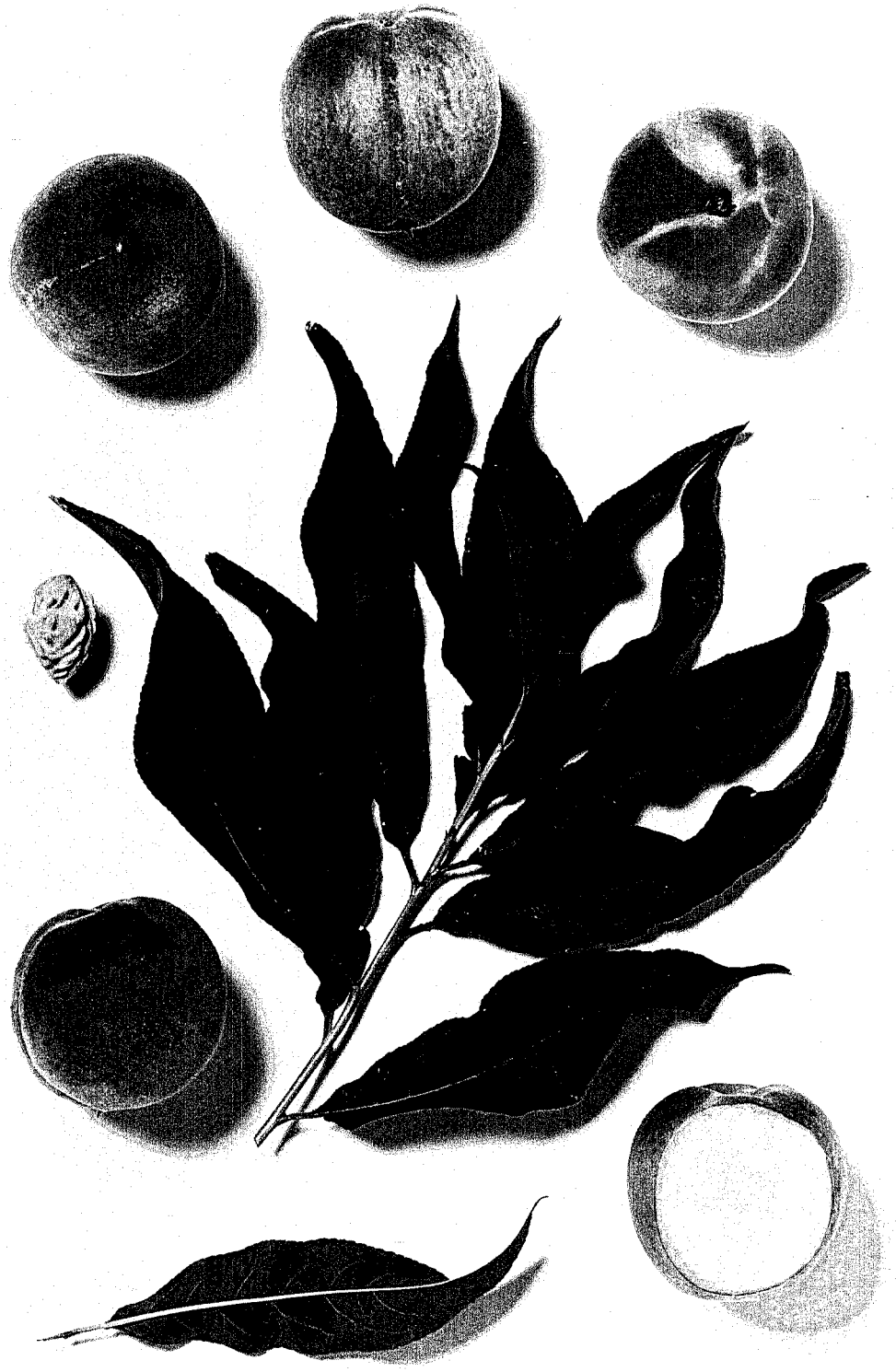

* * * * *